(12) United States Patent
Mason

(10) Patent No.: US 8,096,309 B2
(45) Date of Patent: Jan. 17, 2012

(54) COMPACT DENTAL FLOSSING TOOL

(76) Inventor: Robert Frazer Mason, Bellflower, CA (US)

( * ) Notice: Subject to any disclaimer, the term of this patent is extended or adjusted under 35 U.S.C. 154(b) by 443 days.

(21) Appl. No.: 12/231,260

(22) Filed: Sep. 2, 2008

(65) Prior Publication Data

US 2010/0051052 A1 Mar. 4, 2010

(51) Int. Cl.
*A61C 15/00* (2006.01)
(52) U.S. Cl. .................................................. 132/324
(58) Field of Classification Search ........... 132/323–329
See application file for complete search history.

(56) References Cited

U.S. PATENT DOCUMENTS

| 5,251,651 A * | 10/1993 | Mason ........................ 132/326 |
| 5,348,032 A * | 9/1994 | Mason ........................ 132/325 |
| 2003/0230320 A1* | 12/2003 | Guo ............................ 132/324 |

* cited by examiner

*Primary Examiner* — Rachel Steitz
(74) *Attorney, Agent, or Firm* — George P. White

(57) ABSTRACT

An improved dental flossing tool having a handle portion to mount a spool of dental floss that is easily drawn from an elongated flexible tip covered by a soft resilient sleeve sealing the tip and to provide smooth flossing without any annoying clicking sounds against ones teeth and easily reaching the molar teeth in the back of ones mouth while massaging the gum line at the same time.

16 Claims, 1 Drawing Sheet

COMPACT DENTAL FLOSSING TOOL

FIELD OF INVENTION

This invention relates to dental flossing tools and is particularly directed to a sealed flexible tip flossing tool that assists in reaching each and every tooth with ease and comfort and for preventing moisture and germs from entering the tip that could cause serious infection problems.

PRIOR ART

It has been known for a long time that the flossing of teeth is necessary technique for dental health and for avoiding cavities along with other oral problems with the teeth and gums.

Sadly, many people do not floss their teeth mainly because of the difficulty in holding the floss in their hands and trying to put their fingers into their mouths and then trying to force the floss between adjacent teeth. This difficulty along with the fact that many people are not at home where they can wash their hands for good hygiene could cause many oral problems Some prior art has a strand of floss stretching across two fingers which is not practical for the simple reason that teeth do not come together with both sides of each tooth having a flat surface. Therefore when one forces a strand between two teeth the strand of floss can break though snapping against the gum line which could cause serious gum problems.

A specific object of the present invention is to provide an improved dental flossing tool comprising a single elongated tip at one end of a handle portion which contains a supply of dental floss. A strand of floss passes through the tool to exit out the tip to grasp onto with the free hand while the other hand holds the tool. The tip of the tool does all the reaching to each and every tooth. Placing the tip of the tool next the teeth to be flossed and with one finger, wiggle the strand of floss in between. Each tooth can be flossed with an up and down motion or a see-saw motion.

These and other objects and features of the present invention will be apparent from the present invention with reference to the figures of the accompanying drawings.

BRIEF SUMMARY AND OBJECTS OF INVENTION

In accordance with the present invention, a single tool is provided having a handle portion that holds a spool of dental floss. The handle has an extended flexible tip that is covered by a soft resilient sleeve sealing the tip preventing moisture and germs from entering while allowing the floss to pass forward to exit out said tip. Two hands are used, one to hold the tool and the other to hold the free end of the floss. To floss each tooth you place the tip of the tool next to the teeth to be floss and with your free hand using only one finger, wiggle the strand of floss between the two teeth. Now one has the option of flossing each surface of each tooth with an up and down action or a see-saw action cleaning below the gum line with the soft tip massaging the gum line.

Prior art has many disadvantages permitting exposure of the floss prior to use and the uncomfortable use of these tools being made of plastic as they click and click against your teeth throughout the flossing process.

Also many flossing tools stretch the floss taut between two fingers. There is never a straight line between the surface where two teeth come together. Therefore, when forcing the taut floss between the teeth, the floss can snap in and hit against the gum line causing bleeding and other oral problems.

Also if a flossing tool does nor flex, like new tooth brushes it's like putting a stick in your mouth Another additional object of the present invention is to provide an improved dental flossing tool containing a supply of floss and having means to withdraw a strand of floss in any desired length.

DETAILED DESCRIPTION OF THE DRAWINGS

DETAILED DESCRIPTION OF THE INVENTION

Figure 1:
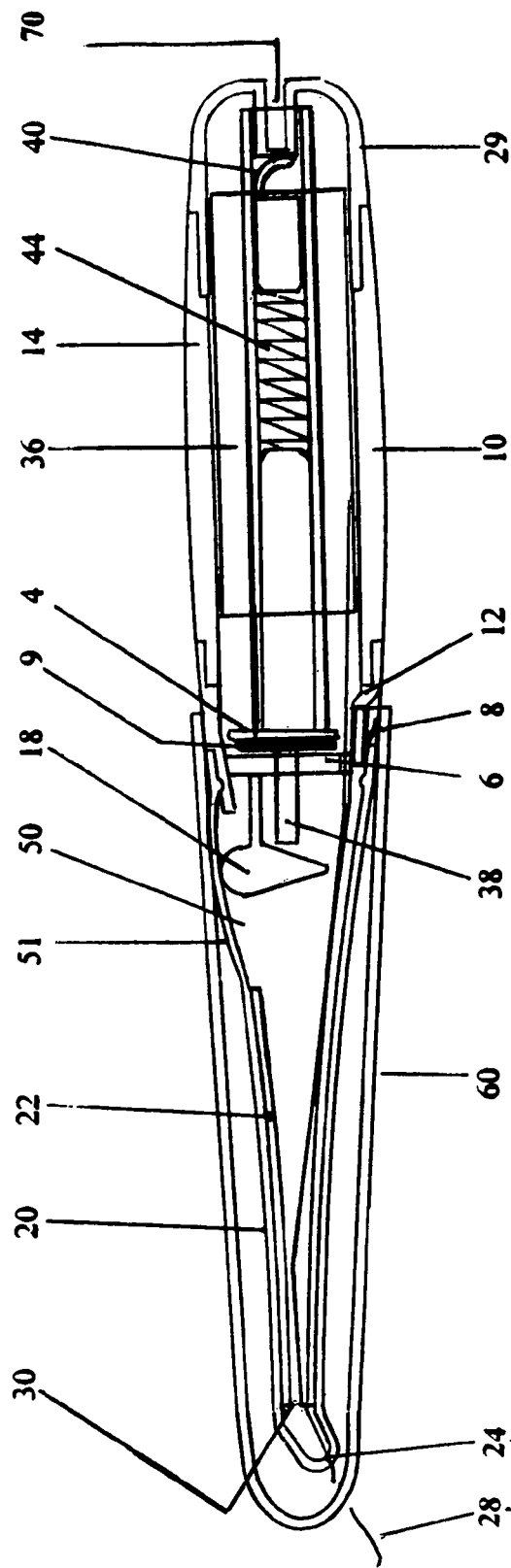
FIG. 1 is a longitudinal section through this dental tool embodying the present invention showing the floss traveling through a hollow tip.
Figure 3:
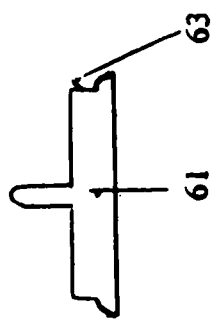
FIG. 3 is a side view of a stand to secure the flossing tool of the present invention when the tool is not in use.
Figure 2:
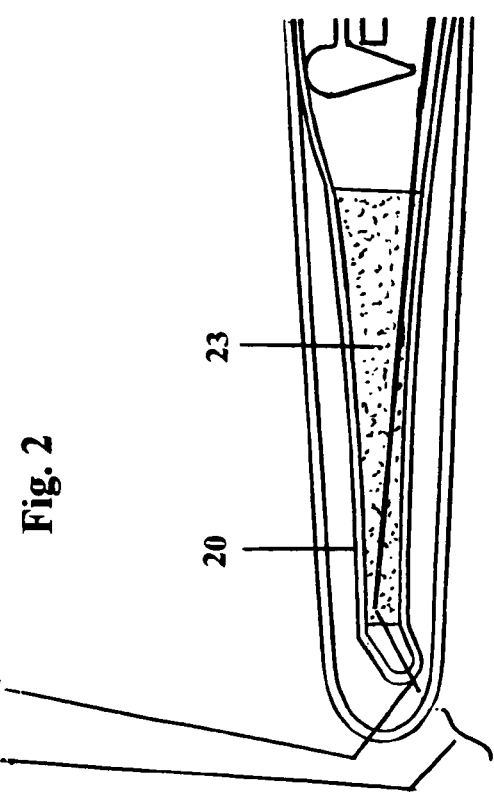
FIG. 2 is a longitudinal section of an alternative tip showing the floss traveling on the outer surface of the tip.

In that form of the present invention chosen for purposes of illustration in FIG. 1, a dental flossing tool, indicated generally at 10, is shown having a main housing 12, a rear handle housing 14 and an extended tip 22 with an opening 30 for the floss 28 to pass through. FIG. 2 shows a non hollow tip 23 with the floss 28 traveling on the outer surface of the tip 23 and also covered by a soft resilient covering 20. Note: The tip 22 or 23 can be of any shape or design since its covered and sealed. The main housing 12 is generally cylindrical with a slender extended flexible tip 22 or 23 projecting forwardly from the cylinder portion 12, and the tip 22 or 23 is covered by a soft resilient sleeve 20, sealing the tip 22 or 23 and the sleeve having an opening 24 at the extreme forward end to permit passage of a strand of dental floss 28, to be dispensed.

The handle 14 is removable to refill with a spool of floss 36 and the rear cap 29 is also removable to refill with more floss. An opening 50 is formed in the cylindrical portion of the main housing 12, and a resilient cover 51 seals the opening 50 to prevent atmospheric moisture from entering the housing 12 and be sufficiently flexible to cause movement of the arm 18 against the forward end of shaft 38 urging shaft 38 to move toward the rear, disengaging soft latex washer 9 on the disc 4 that is formed on the shaft 38 from the locking means 6 allowing the floss spool 36 to rotate so the floss can pass through to exit out the soft resilient sleeve opening 24.

The arm 18 is urged into its normal locking position by pulling on the floss strand 28 and in turn urging the floss spool 36 forward. Also tension means 40 and/or 44 assist in urging said shaft 38 forward and into said locking position.

The soft latex washer 9 on the disc 4 engages frictionally with the locking means 6 to stop any rotation of the floss spool 36 and will consequently prevent movement of the floss strand 28.

To perform the flossing operation, the user holds the dental flossing tool 10 in one hand and with the other hand grasps the free end of the floss strand. The user then presses one finger against the resilient cover 51 to force the arm 18 down and in turn urging the shaft 38 toward the rear disengaging the soft latex washer 9 on the disc 4 from the locking means 6 in the housing. The user may then pull the strand of floss 28 to draw any desired length from the floss supply through the opening in the sleeve 24, of the flexible tip 22. When the strand of floss 28 is at the desired length, the user removes their finger from the resilient cover 51 which allows the shaft 38 to move forward allowing the soft latex washer 9 to engage locking means 6 to prevent rotation of the floss spool 36 of dental floss.

Holding the free end of the floss strand 28 in one hand and holding the dental flossing tool 10 in the other hand, the user may then freely manipulate the strand of floss 28 into the recess between adjacent teeth and can floss with an up and down action or a see-saw movement flossing all surfaces of each tooth including massaging the gums at the same time with the soft tip of the sleeve 20.

Upon completion of the flossing operation, the free strand of floss 28 is severed by suitable means 8 such as seen in FIGS. 1 and 63 as seen in FIG. 2. When this is done, the locking means 6 will prevent any undesired movement of the floss strand 28. The cap 60 can now be placed over the tip 22 or 23 of the tool. If one is at home in their bathroom they can place the flossing tool 10 in a separate holding fixture 61 assisted by an opening 70 at the rear of the handle 14 for later use.

Obviously, numerous other variations and modifications can be made without departing from the sprit of the present invention. Therefore, it should be clearly understood that the forms of this present invention described above and shown in the figures of the accompanying drawings are for illustration only and are not intended to limit the scope of the present invention.

What I claim as my invention is:

1. A dental flossing tool comprising;
   a) a hollow handle for housing a supply of dental floss, and
   b) a spool of floss mounted within said handle, and said handle having an extended tip, and said tip being formed having flexibility;
   c) a resilient sleeve sealingly covering said tip and having an aperture permitting a strand of floss from said floss supply to exit from said tool: the resiliency of the sleeve at the aperture being tight enough around the strand to prevent moisture and germs from entering along the strand of floss and past the covering sleeve, and
   d) means for locking located within said tool for removal of said floss strand from said floss supply in various frictionally locked lengths as desired.

2. The flossing tool of claim 1 with the flexible tip being hollow such as to allow said strand of floss from said floss supply to pass through the terminus of the tip.

3. The flossing tool of claim 1 such that in threading the strand of floss through said aperture said aperture is stretched open allowing said strand of said floss to exit through; and said aperture then collapses around said strand of floss sealingly such as to prevent moisture and germs from entering said tip.

4. The flossing tool of claim 1 further comprising said tip being removably mounted to said tool.

5. The flossing tool of claim 3 with said sleeve being removably attached to said handle.

6. The flossing tool of claim 1 with the sleeve and tip being constituted by material medically approved for oral use.

7. The flossing tool of claim 1 with said handle being removably mounted to said tool for refilling said tool with a new supply of floss.

8. The flossing tool of claim 1 with said handle portion having a removable rear cap for refilling said tool; and with said rear cap being formed to allow said tool to be mated to a holding fixture when said tool is not in use.

9. The flossing tool of claim 1 with said tool formed having a removeably attached floss cut-off mount.

10. The flossing tool of claim 1 with said tool being formed to operate silently when advancing said floss and when locking movement of said floss.

11. The flossing tool of claim 1 further comprising a separate holding fixture suitably shaped and configure to secure said tool when said tool is not being used.

12. The flossing tool of claim 11 where said holding fixture has a removably mounted cutter blade suitably shaped and configured to cut said floss strand.

13. A dental flossing tool comprising:
   a hollow handle for housing a supply of dental floss, and
   a spool of floss mounted within said handle, and said handle having an extended tip, and said tip being formed having flexibility with resilient means sealing said tip preventing moisture and germs from entering, and said means having an aperture permitting a strand of floss from said floss supply to travel forward to exit from said tool, and
   means for locking located within said tool for removal of said floss strand from said floss supply in various frictionally locked lengths as desired; and further with said means for locking being a shaft carrying the spool of dental floss, and said shaft having a tensioner urging said shaft forward to said locked position, and an arm moveable between said locked position out of engagement with said shaft and an unlocked position frictionally engaging said shaft moving said shaft toward the rear of said tool permitting said spool of floss to rotate allowing said strand of said floss to be drawn from said tip of said tool, and an opening formed in said tool adjacent to an arm release portion, the opening having a resilient cover sealing said opening to prevent moisture from entering said tool, and said cover being sufficiently flexible to permit the user to apply pressure through said resilient cover to move said arm release.

14. The flossing tool of claim 13 with said tensioner being formed on the rear of said shaft urging said shaft forward to said locked position.

15. The flossing tool of claim 13 in said tensioner is a spring urging said shaft to said locked position.

16. The flossing tool of claim 13 wherein said means for locking comprises a soft resilient member mounted on said shaft and said shaft frictionally engaging said resilient member such as to stop rotation of said spool of floss.

* * * * *